Figure 1:
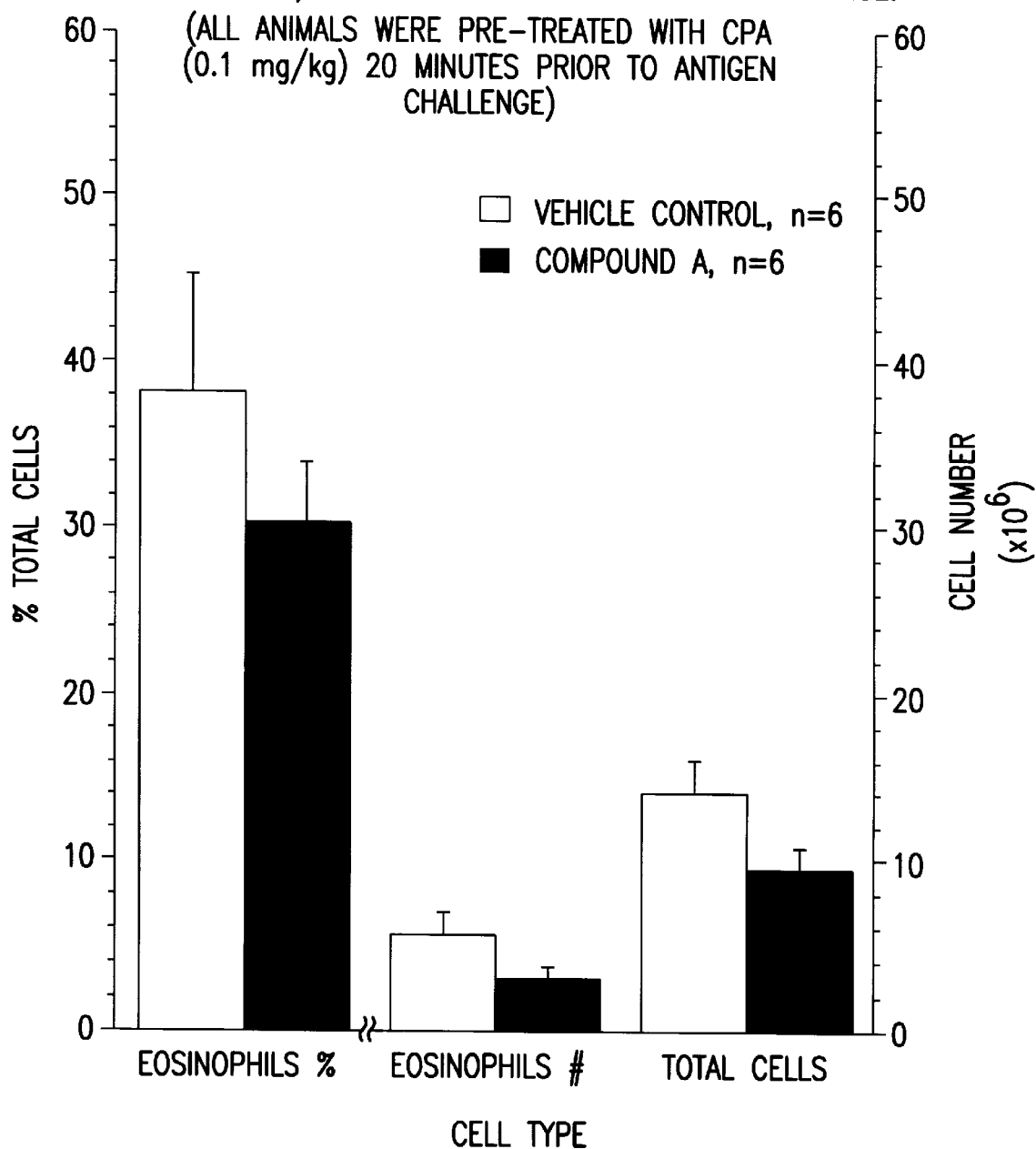

United States Patent [19]
Badger et al.

[11] Patent Number: 6,025,364
[45] Date of Patent: Feb. 15, 2000

[54] METHOD OF TREATING ASTHMA

[75] Inventors: Alison Mary Badger, Bryn Mawr; John Gerald Gleason, Downington, both of Pa.

[73] Assignee: AnorMed, Inc., Langley, Canada

[21] Appl. No.: 09/180,843

[22] PCT Filed: May 15, 1997

[86] PCT No.: PCT/IB97/00688

§ 371 Date: Jan. 15, 1999

§ 102(e) Date: Jan. 15, 1999

[87] PCT Pub. No.: WO97/44030

PCT Pub. Date: Nov. 27, 1997

Related U.S. Application Data

[60] Provisional application No. 60/017,889, May 17, 1996.

[51] Int. Cl.$^7$ .......................... A61K 31/44; A61K 31/40
[52] U.S. Cl. .......................... 514/278; 514/409; 514/183; 514/212
[58] Field of Search .................................. 514/183, 2–12, 514/409, 278

[56] References Cited

U.S. PATENT DOCUMENTS 4,963,557  10/1990  Badger et al. .......................... 514/278
5,482,959   1/1996  Badger .................................. 514/409

FOREIGN PATENT DOCUMENTS

92/04899  4/1992  WIPO .
95/03041  2/1995  WIPO .
95/03042  2/1995  WIPO .
95/03049  2/1995  WIPO .

OTHER PUBLICATIONS

Anderson et al., "An in vivo model for measuring antigen-–induced SRS–A–Mediated Bronchoconstriction and Plasma SRS–A–Levels in the Guinea–Pig", *Br. J. Pharmac.* (1983), 78, 67–74.

*Primary Examiner*—Phyllis G. Spivack
*Attorney, Agent, or Firm*—Morrison & Foerster, LLP

[57] ABSTRACT

Invented is a method of treating asthma, in mammals, including humans, which comprises administering to such human an effective amount of a substituted azaspirane.

7 Claims, 1 Drawing Sheet

METHOD OF TREATING ASTHMA

This application claims benefit of Provisional Application No. 60/017,889 filed May 17, 1996.

This invention relates to a method of treating asthma, in mammals, including humans, which comprises administering to such human an effective amount of a substituted azaspirane.

Badger et al U.S. Pat. No. 4,963,557 (Badger I) discloses compounds of the Formula I

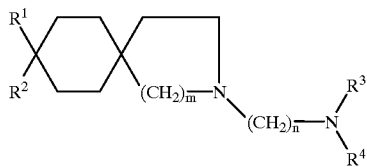

wherein:
n is 3–7;
m is 1 or 2;
$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms:
$R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms;
or a pharmaceutically acceptable salt or hydrate or solvate thereof.

Badger I discloses compounds of Formula I as a class of novel compounds which induce an immunomodulatory effect which is characterised by the stimulation of suppressor cell activity. Particular disease states treatable with the compounds of Formula I, as disclosed in Badger I, are: rheumatoid arthritis, systemic lupus erythematosis, multiple sclerosis, acute transplantation/graft rejection, myasthenia gravis, progressive systemic sclerosis, multiple myeloma, atopic dermatitis, hyperimmunoglobin E, hepatitis B antigen negative chronic active hepatitis, Hasimoto's thyroiditis, Familial Mediterranean fever, Grave's disease, autoimmune hamolytic anaemia, primary biliary cirrhosis and inflammatory bowel disease.

International Application No. PCT/US91/06778, having the International Publication No. WO 92/04/899 and an International Publication Date of Apr. 2, 1992, discloses compounds of the above Formula I as being useful in treating a disease state which is exacerbated or caused by excessive glucose levels.

International Application No. PCT/US92/01283, having the International Publication No. WO 92/14462 and an International Publication Date of Sep. 3, 1992 (Badger II), discloses the compounds of the above Formula I as being useful in the inhibition of cytokines. Preferred disease states treatable with the compounds of Formula I, as disclosed in Badger II, are: increased bone resorption (including osteoporosis and Paget's disease), endotoxic shock, cachexia secondary to acquired immune deficiency syndrome (AIDS), AIDS and matrix.

U.S. Pat. No. 5,482,959 discloses compounds of the above Formula I as being useful in delaying AIDS in HIV infected individuals.

International Application No. PCT/US94/08275, having the International Publication No. WO 95/03041 and an International Publication Date of Feb. 2, 1995, International Application No. PCT/US94/08274, having the International Publication No. WO 95/03049 and an International Publication Date of Feb. 2, 1995, and International Application No. PCT/US94/08276, having the International Publication No. WO 95/03042 and an International Publication Date of Feb. 2, 1995, disclose the compounds of the above Formula I as being useful in various mechanisms of HIV inhibition.

None of the above references disclose the compounds of Formula I as being useful in treatment of asthma.

This invention relates to a method of treating asthma, in mammals, including humans, which comprises administering to a subject in need thereof an effective amount of a compound of the Formula I

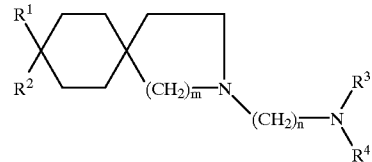

wherein:
n is 3–7;
m is 1 or 2;
$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;
$R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms;
or a pharmaceutically acceptable salt or hydrate or solvate thereof.

In the alternative this invention relates to the use of a compound of Formula I

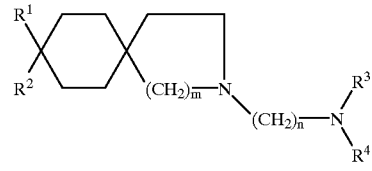

wherein:
n is 3–7;
m is 1 or 2;
$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;
$R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms;
or a pharmaceutically acceptable salt or hydrate or solvate thereof; in the manufacture of a medicament for use in treating asthma in mammals, including humans.

The preparation of compounds of Formula I and pharmaceutically acceptable salts, hydrates and solvates and formulations thereof is disclosed in U.S. Pat. No. 4,963,557, the entire disclosure of which is hereby incorporated by reference.

A preferred compound used in the novel method is the dimaleate salt of a compound of Formula I where $R^1$ and $R^2$ are propyl, $R^3$ and $R^4$ are methyl, m is 1 and n is 3 which is N,N-dimethyl-8,8-dipropyl-2azaspiro[4.5]decane-2-propanamine dimaleate.

A particularly preferred compound used in the novel method is the dimaleate salt of a compound of Formula I where $R^1$ and $R^2$ are propyl, $R^3$ and $R^4$ are ethyl, m is 1 and n is 3 which is N,N-diethyl-8,8-dipropyl-2-azaspiro[4.5]decane-2-propanamine dimaleate.

A particularly preferred compound used in the novel method is the dimaleate salt of a compound of Formula I where $R^1$ and $R^2$ are propyl, $R^3$ and $R^4$ are joined together with the nitrogen to form a piperidine ring, m is 1 and n is 3 which is 8,8-dipropyl-2-azaspiro[4.5]decane-2-piperidinopropyl dimaleate.

The above dimaleate salts can be prepared by dissolving the base in an appropriate organic solvent, such as de-oxygenated ethyl acetate, with subsequent addition of two or more equivalents of maleic acid.

By the term "treating" as used herein is meant prophylactic or therapeutic therapy.

The invention discloses compounds of Formula I and pharmaceutically acceptable salts or hydrates or solvates thereof as being useful for treating asthma in mammals, including humans.

The compounds of Formula I are tested for their ability to treat asthma in the assay described in Anderson, *Br. J. Pharmac.* (1983), 78, 67–74.

This invention relates to a method of treating asthma which comprises administering to a subject in need thereof an effective amount of a compound of Formula I or a pharmaceutically acceptable salt or hydrate or solvate thereof. The invention also relates to the use of a compound of Formula I or a pharmaceutically acceptable salt or hydrate or solvate thereof in the manufacture of a medicament for use in treating asthma. A compound of Formula I or a pharmaceutically acceptable salt or hydrate or solvate thereof can be administered to such subject in a conventional dosage form prepared by combining a compound of Formula I or a pharmaceutically acceptable salt or hydrate or solvate thereof, with a conventional pharmaceutically acceptable carrier or diluent according to known techniques, such as those described in Badger I, U.S. Pat. No. 4,963,557.

It will be recognized by one skilled in the art that the form and character of the pharmaceutically acceptable carrier or diluent is dictated by the amount of active ingredient with which it is to be combined, the route of administration and other well-known variables. A compound of Formula I ("Active Ingredient") or a pharmaceutically acceptable salt or hydrate or solvate thereof is administered to a subject in need of treatment for asthma in an amount sufficient to prevent or alleviate the asthmatic condition.

The route of administration of the Formula I compound is not critical but is usually oral or parenteral, preferably oral.

The term parenteral as used herein includes intravenous, intramuscular, subcutaneous, intranasal, intrarectal, transdermal, intravaginal or intraperitoneal administration. The subcutaneous and intramuscular forms of parenteral administration are generally preferred. The daily parenteral dosage regimen will preferably be from about 0.01 mg/kg to about 10 mg/kg of total body weight, most preferably from 0.1 mg/kg to about 1 mg/kg. Preferably, each parenteral dosage unit will contain the active ingredient in an amount of from about 0.1 mg to about 100 mg.

The compounds of Formula I which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose, and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

The daily oral dosage regimen will preferably be from about 0.01 mg/kg to about 10 mg/kg of total body weight. Preferably each oral dosage unit will contain the active ingredient in an amount of from about 0.1 mg to about 100 mg.

While it is possible for an active ingredient to be administered alone, it is preferable to present it as a pharmaceutical formulation.

It will be recognized by one of skill in the art that the optimal quantity and spacing of individual dosages of a compound of Formula I or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, ie, the number of doses of a compound of Formula I or a pharmaceutically acceptable salt or hydrate or solvate thereof given per day and duration of therapy, can be ascertained by those skilled in the art using conventional course of treatment determination tests.

The method of this invention of treating asthma in mammals, including humans, comprises administering to a subject in need of such treatment an effective amount of a pharmaceutically active compound of the present invention.

The invention also provides for the use of a compound of Formula I in the manufacture of a medicament for use in treating asthma in mammals, including humans.

The invention also provides for a pharmaceutical composition for use in treating asthma in mammals, including humans which comprises a compound of Formula I and a pharmaceutically acceptable carrier.

The invention also provides for a process for preparing a pharmaceutical composition containing a pharmaceutically acceptable carrier or diluent and a compound of Formula I which comprises bringing the compound of Formula I into association with the pharmaceutically acceptable carrier or diluent.

No unacceptable toxicological effects are expected when compounds of the invention are administered in accordance with the present invention.

In addition, the compounds of the present invention can be co-administered with further active ingredients known to treat asthma.

Without further elaboration, it is believed that one skilled in the art can, using the preceding description, utilise the present invention to its fullest extent. The following examples are, therefore, to be construed as merely illustrative and not a limitation of the scope of the present invention in any way.

EXAMPLE 1

Capsule Composition

An oral dosage form for administering Formula I compounds is produced by filing a standard two-piece hard gelatin capsule with the ingredients in the proportions shown in Table I, below.

TABLE 1

| Ingredients | Amounts |
| --- | --- |
| N,N-diethyl-8,8-dipropyl-2-azaspiro[4.5]-decane-2-propanamine dimaleate | 25 mg |
| Lactose | 55 mg |
| Talc | 16 mg |
| Magnesium Stearate | 4 mg |

EXAMPLE 2

Injectable Parenteral Composition

An injectable form for administering Formula I compounds is produced by stirring 1.5% by weight of N,N-diethyl-8,8-dipropyl-2-azaspiro[4.5]decane-2-propanamine dimaleate in 10% by volume propylene glycol in water.

EXAMPLE 3

Tablet Composition

The sucrose, calcium sulphate dihydrate and Formula I compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| N,N-diethyl-8,8-dipropyl-2-azaspiro[4.5]decane-2-propanamine dimaleate | 20 mg |
| Calcium sulphate dihydrate | 30 mg |
| Sucrose | 4 mg |
| Starch | 2 mg |
| Talc | 1 mg |
| Stearic acid | 0.5 mg |

EXAMPLE 4

Inhibition of Antigen-Inducted Airway Eosinophil Influx

The inhibition of antigen-induced airway eosinophil influx was demonstrated for the following compound: N,N-diethyl-8,8-dipropyl-2-azaspiro[4.5]decane-2-propanamine dihydrochloride (Compound A). The results are shown in FIG. 1 (Compound A).

While the above descriptions and examples fully describe the invention and the preferred embodiments thereof, it is understood that the invention is not limited to the particular disclosed embodiments coming within the scope of the following claims.

We claim:

1. A method to treat asthma, in mammals which method comprises administering to a mammal in need of such treatment an effective amount of a compound of formula

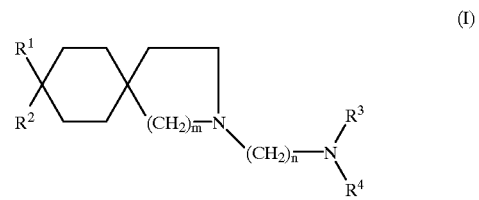

(I)

wherein;

n is 3–7;

m is 1 or 2;

each of $R^1$ and $R^2$ is independently hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;

each of $R^3$ and $R^4$ is independently hydrogen or straight chain alkyl having 1–3 carbon atoms; or $R^3$ and $R^4$ are joined together with the nitrogen atom to form a heterocyclic group having 5–8 atoms;

or a pharmaceutically acceptable salt or hydrate or solvate thereof.

2. The method of claim 1 wherein the compound is N,N-diethyl-8,8-dipropyl-2-azaspiro[4.5]decane-2-propanamine; or a pharmaceutically acceptable salt, hydrate or solvate thereof.

3. The method of claim 1 wherein the compound is administered orally.

4. The method of claim 3 wherein from about 0.01 mg/kg to about 10 mg/kg of compound is administered per day.

5. The method of claim 1 wherein the compound is administered parenterally.

6. The method of claim 5 wherein from about 0.01 mg/kg to about 10 mg/kg of compound is administered per day.

7. The method of claim 1 wherein the mammal is a human.

* * * * *